(12) United States Patent
Fung et al.

(10) Patent No.: US 8,653,296 B2
(45) Date of Patent: Feb. 18, 2014

(54) METHOD FOR PREPARING ESTER OF CYCLOHEXANE POLYCARBOXYLIC ACID FROM ESTER OF BENZENE POLYCARBOXYLIC ACID

(75) Inventors: Dein-Run Fung, Taipei (TW); Jung-Jen Chuang, Taipei (TW); Chung-Yu Chen, Taipei (TW); Heng-Hua Hsiao, Taipei (TW)

(73) Assignee: Nan Ya Plastics Corporation, Taipei (TW)

( * ) Notice: Subject to any disclaimer, the term of this patent is extended or adjusted under 35 U.S.C. 154(b) by 193 days.

(21) Appl. No.: 13/362,003

(22) Filed: Jan. 31, 2012

(65) Prior Publication Data
US 2012/0226069 A1 Sep. 6, 2012

(30) Foreign Application Priority Data
Mar. 1, 2011 (TW) .............................. 100106605 A

(51) Int. Cl.
*C07C 61/09* (2006.01)
(52) U.S. Cl.
USPC .......................................... 560/127; 560/126

(58) Field of Classification Search
USPC .................................................. 560/126, 127
See application file for complete search history.

(56) References Cited

U.S. PATENT DOCUMENTS 2,070,770 A * 2/1937 Amend .......................... 560/127

* cited by examiner

*Primary Examiner* — Kamal Saeed
*Assistant Examiner* — Janet L Coppins
(74) *Attorney, Agent, or Firm* — Bacon & Thomas, PLLC

(57) ABSTRACT

A method for preparing esters of cyclohexane polycarboxylic acids from esters of benzene polycarboxylic acids makes improvement to hydrogenation of esters of benzene polycarboxylic acids by using a reaction tank having a gas-introducing mixer capable of extracting and exhausting air and stirring to hydrogenate an ester of a benzene polycarboxylic acids into an ester of a cyclohexane polycarboxylic acid in the presence of a hydrogenation catalyst; resulted in that the method advantageously minimizes the operational pressure for hydrogenating esters of benzene polycarboxylic acids and significantly lowers the reaction temperature for hydrogenation while effectively improving the yield of esters of cyclohexane polycarboxylic acids made from the esters of the benzene polycarboxylic acids.

12 Claims, 2 Drawing Sheets

METHOD FOR PREPARING ESTER OF CYCLOHEXANE POLYCARBOXYLIC ACID FROM ESTER OF BENZENE POLYCARBOXYLIC ACID

BACKGROUND OF THE PRESENT INVENTION

1. Field of the Invention

The present invention relates to methods for preparing esters of cyclohexane polycarboxylic acids, and more particularly, to a method for preparing esters of cyclohexane polycarboxylic acids by hydrogenating esters of benzene polycarboxylic acids.

2. Description of Prior Art

In the field of plasticization for PVC, esters of benzene polycarboxylic acids are widely used as the plasticizer that endows PVC products with improved softness and toughness. However, such esters of benzene polycarboxylic acids as dibutyl phthalate, diisooctyl phthalate (DIOP) and diisononyl phthalate (DINP) are environmental hormone harmful to human health and have been legally limited to or prohibited from use in many countries, while esters of cyclohexane polycarboxylic acids are instead used as the plasticizer for PVC.

Conventionally, esters of cyclohexane polycarboxylic acids have been made through either esterification or hydrogenation. For preparing esters of cyclohexane polycarboxylic acids through esterification, a cyclohexane polycarboxylic acid or a cyclohexane polycarboxylic anhydride is esterified with an aliphatic monohydric alcohol. However, since cyclohexane polycarboxylic acids and cyclohexane polycarboxylic anhydrides are expensive, this process is unfavorable to industrial production.

On the other hand, preparing esters of cyclohexane polycarboxylic acids through hydrogenation, as taught by U.S. Pat. No. 2,070,770, involves hydrogenating an ester of a benzene polycarboxylic acid in the presence of a hydrogenation catalyst under a raised pressure.

As shown in FIG. 1, in a known hydrogenation process for making esters of cyclohexane polycarboxylic acids, an apparatus implemented has a hydrogenation tank 10, provided therein with a traditional impeller mixing device 20. The impeller mixing device 20 uses a rotatory shaft 21 to drive vanes 22 at the terminal of the rotatory shaft 21 to rotate and thereby stir a solution of an ester of a benzene polycarboxylic acid (hereinafter referred to as the reaction liquid) 30. While the vanes 22 rotate, a hydrogen nozzle 60 immersed in the reaction liquid 30 introduce a high-pressure hydrogen gas into the reaction liquid 30, so that the rotating vanes 22 promote the contact between hydrogen gas and the reaction liquid 30, making the reaction liquid 30 get hydrogenated in the presence of the hydrogen gas and a catalyst, thereby obtaining the desired ester of the cyclohexane polycarboxylic acid.

Such a hydrogenation tank 10, however, is less effective in increasing the contact between hydrogen gas and the reaction liquid 30, so the yield of the ester of the cyclohexane polycarboxylic acid as a production of hydrogenation is relatively low. For improving the productivity, the hydrogenation tank 10 has to be made for high-pressure operation and thus unavoidably requires higher costs in fabrication, operation and maintenance, being unfavorable to industrial production as well.

SUMMARY OF THE INVENTION

The present invention provides a method for preparing ester of cyclohexane polycarboxylic acid by hydrogenating ester of benzene polycarboxylic acid under a low-temperature and low-pressure environment, resulted in that a hydrogenation tank employed in the method of the present invention is not necessarily to be made for high-pressure operation and the costs in fabrication, operation and maintenance of the hydrogenation tank is effectively reduced.

The method of the present invention advantageously minimizes the operational pressure for hydrogenating esters of benzene polycarboxylic acids and significantly lowers the reaction temperature for hydrogenation while effectively improving the yield of esters of cyclohexane polycarboxylic acids made from the esters of the benzene polycarboxylic acids.

The method of the present invention is suitably applied for preparing ester of cyclohexane polycarboxylic acid, which comprises steps of:

a) preparing a hydrogenation tank that is provided therein with a gas-introducing mixer capable of extracting and exhausting air and stirring;

b) placing a reaction liquid made from an ester of the benzene polycarboxylic acid into the hydrogenation tank;

c) adding a hydrogenation catalyst that is one selected from a ruthenium catalyst, a palladium catalyst, a platinum catalyst and a rhodium catalyst in an amount of 0.1-5.0 wt % based on the ester of the benzene polycarboxylic acid;

d) introducing a hydrogen gas with a pressure of 5-60 $kg/cm^2$;

e) starting the gas-introducing mixer to make a hollow rotatory shaft of the gas-introducing mixer and vanes attached to a terminal of the rotatory shaft rotate at a predetermined speed to let the hydrogen gas be drawn into the hollow rotatory shaft through air-extracting holes formed on the hollow rotatory shaft above a liquid surface of the reaction liquid, and then exhausted out from air-exhausting holes formed on the hollow rotatory shaft at a location immersed in the reaction liquid, for having the hydrogen gas evenly distributed over the reaction liquid as the vanes stirring the reaction liquid;

f) performing hydrogenation at 100-200° C. for 2 to 5 hours to hydrogenate the ester of the benzene polycarboxylic acid into the ester of the cyclohexane polycarboxylic acid;

g) after the hydrogenated reaction, cooling the reaction liquid to the room temperature, filtering out the catalyst and optionally further removing the solvent to obtain the ester of the cyclohexane polycarboxylic acid with a yield of 99.0-99.995%.

The present invention differently equips a hydrogenation tank with a gas-introducing mixer capable of extracting and exhausting air and stirring, so as to achieve the following objectives:

1. The contact between hydrogen gas and the reaction liquid is improved without increasing the operational pressure;

2. The reaction liquid to be hydrogenated containing a high level of dissolved hydrogen, so the hydrogenation catalyst is made highly active and thereby speeds up hydrogenation; and 3. Hydrogenation can be performed at a relatively low temperature, so as to significantly reduce the costs for building up and maintaining the hydrogenation tank, while the yield of the ester of the cyclohexane polycarboxylic acid is improved, being economically beneficial.

BRIEF DESCRIPTION OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE PREFERRED EMBODIMENTS

Figure 1:
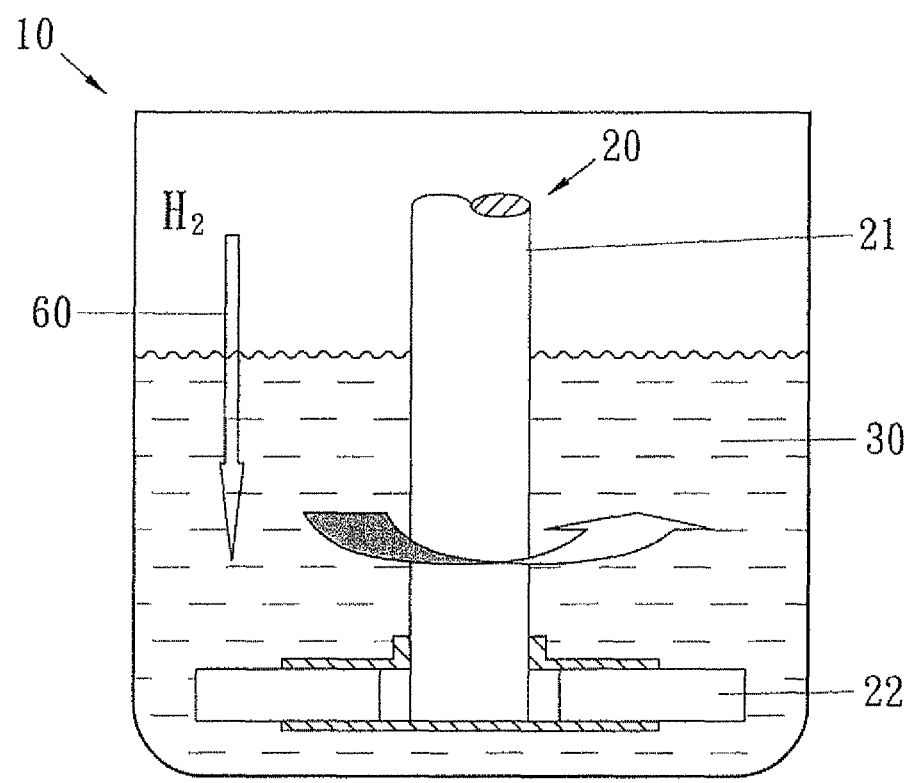
FIG. 1 is a schematic drawing of a conventional hydrogenation tank for operating under high pressure.
Figure 2:
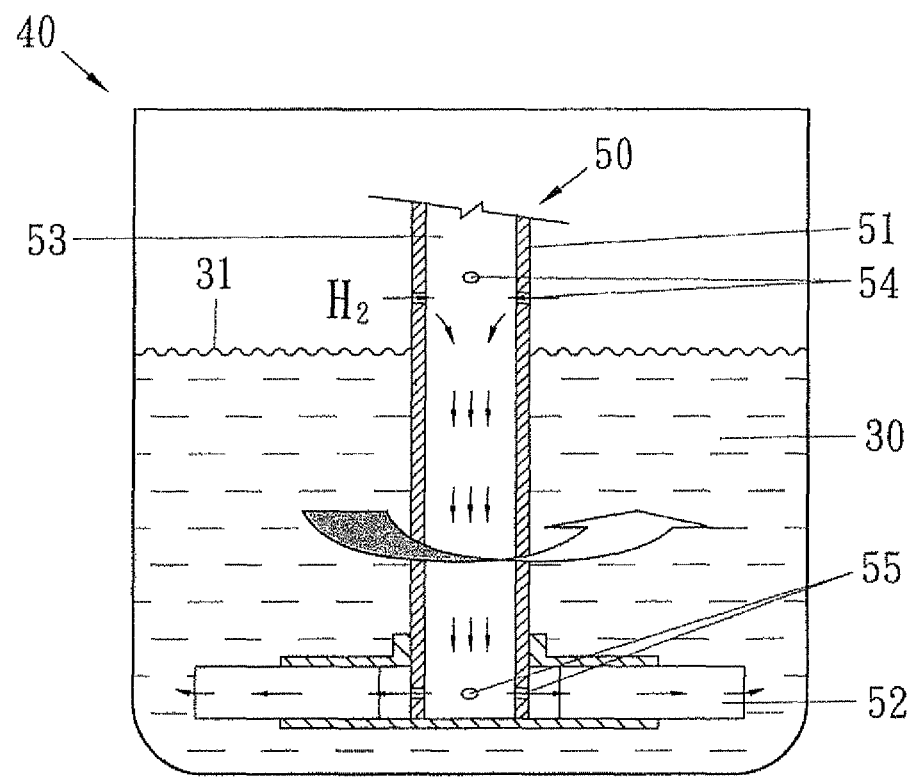
FIG. 2 is a schematic drawing of the inventive hydrogenation tank for operating under low pressure and low temperature.

Referring to FIG. 2, as disclosed by the present invention, the hydrogenation tank 40 is a drum-like, air-tight, high-pressure vessel, with a height/diameter ratio of 0.4-3.0, for hydrogenating esters of benzene polycarboxylic acids or mixtures made from esters of benzene polycarboxylic acids into esters of cyclohexane polycarboxylic acids. According to the present invention, an ester of a benzene polycarboxylic acid or a mixture made form an ester of a benzene polycarboxylic acid may be hydrogenated in a batch, semi-batch, continuous basis. The ester of the benzene polycarboxylic acid and the mixture of the ester of the benzene polycarboxylic acid are herein generally called the "ester of the benzene polycarboxylic acid".

In the hydrogenation tank 40 of the present invention, there is a gas-introducing mixer 50, which is capable of extracting and exhausting air and stirring, for enhancing the activity of the hydrogenation catalyst and speeding up hydrogenation of the ester of the benzene polycarboxylic acid. Therefore, the hydrogenation tank 40 of the present invention allows hydrogenation of the ester of the benzene polycarboxylic acid performed under relatively low pressure and low temperature, while improving the yield of a resultant ester of a cyclohexane polycarboxylic acid or a mixture of an ester of a cyclohexane polycarboxylic acid made from the ester of the benzene polycarboxylic acid through hydrogenation. The ester of the cyclohexane polycarboxylic acid and the mixture of the ester of the cyclohexane polycarboxylic acid are herein generally called the "ester of the cyclohexane polycarboxylic acid".

In the hydrogenation tank 40 of the present invention, in addition to the gas-introducing mixer 50, there may be a plate heat exchanger or a coil pipe, for timely removing heat generated as a product of hydrogenation so as to prevent heat accumulation.

The gas-introducing mixer 50 structurally comprises a hollow rotatory shaft 51 and vanes 52 attached to a terminal of the hollow rotatory shaft 51. The hollow rotatory shaft 51 is internally formed as a gas channel 53, for delivering hydrogen gas. The hollow rotatory shaft 51 at its upper part has several air-extracting holes 54 communicated with the gas channel 53. In use, the air-extracting holes 54 are located above a liquid surface 31 of the reaction liquid 30, so that the hydrogen gas can be drawn into the gas channel 53. The hollow rotatory shaft 51 at its lower part further has several air-exhausting holes 55 also communicated with the gas channel 53, for allowing the hydrogen gas drawn into the gas channel 53 to be exhausted out from the air-exhausting holes 54.

The vanes 52 of the gas-introducing mixer 50 may be plate vanes, curved vanes or vanes with grooves.

The hydrogenation catalyst for hydrogenation of the ester of the benzene polycarboxylic acid may be a ruthenium catalyst, a palladium catalyst, a platinum catalyst or a rhodium catalyst. In the present invention, the hydrogenation catalyst is used in an amount of preferably 0.1-5.0 wt %, or more preferably 0.5-1.0 wt %, based on the ester of the benzene polycarboxylic acid.

To prepare the reaction liquid 30 from the ester of the benzene polycarboxylic acid, the ester of the benzene polycarboxylic acid is directly dissolved in a liquid that has been contained in the hydrogenation tank 40 of the present invention, or alternatively, the ester of the benzene polycarboxylic acid is previously made into a solution with a solvent or a thinner, before poured into the hydrogenation tank 40 of the present invention.

To prepare the solution of the ester of the benzene polycarboxylic acid, the solvent or thinner may be a pure component or a mixture, as long as it can be mixed with the ester of the benzene polycarboxylic acid into a harmonious phase, such as an aliphatic alcohol with ten carbon atoms, particularly an aliphatic alcohol with three to six carbon atoms, e.g. isopropanol, butanol, hexanol; or linear or cyclic ethers, such as tetrahydrofuran. The particularly preferable solvent or thinner would be the hydrogenation product of the ester of the benzene polycarboxylic acid, namely the ester of the cyclohexane polycarboxylic acid or the mixtures of the ester of the cyclohexane polycarboxylic acid.

There is no special limitation made to the amount of the solvent or thinner, yet, the amount is preferably to make the solution of the ester of the benzene polycarboxylic acid contains 5 to 95 wt % of the ester of the benzene polycarboxylic acid.

With the gas-introducing mixer 50 and the plate heat exchanger or coil pipe, the hydrogenation tank 40 of the present invention facilitates increasing the yield of the ester of the cyclohexane polycarboxylic acid made from the ester of the benzene polycarboxylic acid through hydrogenation for the reason that the hydrogen gas and the reaction liquid contact well in the hydrogenation tank 40, and the heat generated during hydrogenation can be timely dissipated so that hydrogenation can be performed well without using high pressure and high temperature. Therefore, the reaction takes place in the hydrogenation tank of the present invention at 100-200° C., or preferably 180-200° C. with a pressure of the hydrogen gas at 5-60 kg/cm$^2$, or preferably 20-40 kg/cm$^2$, for 2 to 5 hours.

Although the hydrogenation tank 40 of the present invention in the present as described uses pure hydrogen gas, it is to be appreciated that hydrogen gas containing inert gas is also useful for the purpose of the present invention. However, no matter pure hydrogen gas or hydrogen gas containing inert gas is used, it is important to avoid the gas containing sulfide or carbon monoxide that is harmful to the catalyst.

As shown in FIG. 2, for performing hydrogenation, the reaction liquid 30 is poured into the disclosed hydrogenation tank 40, with the catalyst added in a proper amount and the hydrogen gas introduced. Then the gas-introducing mixer 50 is started. As the hollow rotatory shaft 51 of the gas-introducing mixer 50 drives the vanes 52 to rotate and thereby stir the reaction liquid 30, the hydrogen gas above the liquid surface 31 of the reaction liquid 30 is drawn into the gas channel 53 of the hollow rotatory shaft 51 through the air-extracting holes 54 of the hollow rotatory shaft 51, and then exhausted from the air-exhausting holes 55 at the lower part of the hollow rotatory shaft 51, where, with the assistance of the stir by the vanes 52, the exhaust hydrogen gas is evenly distributed over the reaction liquid 30, so as to improve the contact between the hydrogen gas and the reaction liquid 30. Thereby, the reaction liquid 30 contains a high level of dissolved hydrogen, so the hydrogenation catalyst becomes more active to speed up hydrogenation.

After hydrogenation of the ester of the benzene polycarboxylic acid, the catalyst is filtered out, and the obtained ester of the cyclohexane polycarboxylic acid can be directly put into application or can have the solvent or thinner removed by distillation before use. Therein, the yield of the ester of the cyclohexane polycarboxylic acid is up to 99.0-99.995%.

According to the above description, the present invention discloses a method for preparing esters of cyclohexane polycarboxylic acids from esters of benzene polycarboxylic acids, and the method comprises the following steps:

a) preparing a hydrogenation tank 40 that is provided therein with a gas-introducing mixer 50 capable of extracting and exhausting air and stirring;

b) placing a reaction liquid 30 made from an ester of the benzene polycarboxylic acid into the hydrogenation tank 40;

c) adding a hydrogenation catalyst in an amount of 0.1-5.0 wt % based on the ester of the benzene polycarboxylic acid;

d) introducing a hydrogen gas with a pressure of 5-60 kg/cm$^2$;

e) starting the gas-introducing mixer 50 to make a hollow rotatory shaft 51 of the gas-introducing mixer 50 and vanes 52 attached to a terminal of the rotatory shaft 51 rotate at a predetermined speed so that the hydrogen gas is drawn into the gas channel 53 of the hollow rotatory shaft 51 through air-extracting holes 54 formed on the hollow rotatory shaft 51 above a liquid surface 31 of the reaction liquid 30, and then flowed through gas channel 53 and exhausted out from air-exhausting holes 55 formed on the hollow rotatory shaft 51 immersed in the reaction liquid 30. Finally, the exhausted hydrogen gas is evenly distributed over the reaction liquid 30 as the vanes 52 is stirring the reaction liquid 30;

f) performing hydrogenation at 100-200° C. for 2 to 5 hours, so as to hydrogenate the ester of the benzene polycarboxylic acid into the ester of the cyclohexane polycarboxylic acid;

g) after the hydrogenated reaction, cooling the reaction liquid to the room temperature, filtering out the catalyst and optionally further removing the solvent to obtain the ester of the cyclohexane polycarboxylic acid.

The following examples are provided to illustrate the present invention without limiting the scope of the present invention.

Example 1

Diisononyl phthalate (DINP) was weighted 500 g and placed into a 1 L high-pressure reaction tank with the disclosed gas-introducing mixer to form a reaction liquid. Palladium catalyst with activated carbon as a monomer was added in 5 g. Then hydrogen gas was introduced to 20 kg/cm$^2$ where the pressure was maintained. The reaction tank was started with its stirring shaft rotating at 500 rpm. Then the temperature was increased to 200° C., where the reaction was performed for 4 hours.

After the reaction, the hydrogen gas was cut off and the hydrogen gas inside the reaction tank was exhausted. The reaction liquid was cooled to the room temperature. After having the catalyst filtered out, the reaction product was analyzed. The results are shown in Table 1. The conversion rate of diisononyl phthalate was 100%, and the yield of diisononyl cyclohexane phthalate was 99.99%.

Example 2

The conditions were similar to Example 1, except that diisooctyl phthalate (DIOP) was used instead of diisononyl phthalate and the reaction temperature was set as 180° C. The results are shown in Table 1. The conversion rate of diisooctyl phthalate was 99.98%, and the yield of diisooctyl cyclohexane phthalate was 99.5%.

Example 3

The conditions were similar to Example 1, except that the pressure of the pressure of the hydrogen gas was set at 40 kg/cm$^2$ and the reaction temperature was set as 180° C. The results are shown in Table 1. The conversion rate of diisononyl phthalate was 100%, and the yield of diisononyl cyclohexane phthalate was 99.995%.

Example 4

The conditions were similar to Example 2, except that the pressure of the pressure of the hydrogen gas was set at 40 kg/cm$^2$ and the reaction temperature was set as 150° C. The results are shown in Table 1. The conversion rate of diisooctyl phthalate was 99.20%, and the yield of diisooctyl cyclohexane phthalate was 99.05%.

Example 5

The conditions were similar to Example 2, except that the amount of the palladium catalyst was 2.5 g. The results are shown in Table 1. The conversion rate of diisooctyl phthalate was 99.92%, and the yield of diisooctyl cyclohexane phthalate was 99.45%.

Example 6

The conditions were similar to Example 2, except that the pressure of the hydrogen gas pressure was set as 40 kg/cm$^2$. The results are shown in Table 1. The conversion rate of diisooctyl phthalate was 100%, and the yield of diisooctyl cyclohexane phthalate was 99.9%.

Comparative Example 1

The conditions were similar to Example 1, except that a traditional impeller mixing device without the capability of extracting and exhausting air was used together with a hydrogen nozzle for guiding hydrogen gas to enter the reaction tank below the liquid surface, and that the hydrogen gas pressure was set as 40 kg/cm$^2$. The results are shown in Table 1. The conversion rate of diisononyl phthalate was 95.12%, and the yield of diisononyl cyclohexane phthalate was 94.24%.

Comparative Example 2

The conditions were similar to Example 2, except that a traditional impeller mixing device without the capability of extracting and exhausting air was used together with a hydrogen nozzle for guiding hydrogen gas to enter the reaction tank below the liquid surface, and that the hydrogen gas pressure was set as 60 kg/cm$^2$. The results are shown in Table 1. The conversion rate of diisooctyl phthalate was 95.47%, and the yield of diisooctyl cyclohexane phthalate was 94.45%.

Comparative Example 3

The conditions were similar to Example 1, except that a traditional impeller mixing device without the capability of extracting and exhausting air was used together with a hydrogen nozzle for guiding hydrogen gas to enter the reaction tank below the liquid surface, and that the hydrogen gas pressure was set as 60 kg/cm$^2$. The results are shown in Table 1. The conversion rate of diisononyl phthalate was 97.31%, and the yield of diisononyl cyclohexane phthalate was 96.20%.

Comparative Example 4

The conditions were similar to Example 3, except that a traditional impeller mixing device without the capability of extracting and exhausting air was used together with a hydrogen nozzle for guiding hydrogen gas to enter the reaction tank below the liquid surface. The results are shown in Table 1. The conversion rate of diisononyl phthalate was 96.44%, and the yield of diisononyl cyclohexane phthalate was 95.01%.

Comparative Example 5

The conditions were similar to Example 4, except that a traditional impeller mixing device without the capability of extracting and exhausting air was used together with a hydrogen nozzle for guiding hydrogen gas to enter the reaction tank below the liquid surface. The results are shown in Table 1. The conversion rate of diisooctyl phthalate was 90.52%, and the yield of diisooctyl cyclohexane phthalate was 90.02%.

acids from esters of benzene polycarboxylic acids is effective in improving the yield of diisononyl cyclohexane phthalate.

2. Example 3 adopted the reaction conditions of Example 1, except that the hydrogen gas pressure was doubled to 40 kg/cm$^2$, and the reaction temperature was reduced to 180° C. The resultant conversion rate of diisononyl phthalate was also the highest, 100%, and the yield of diisononyl cyclohexane phthalate was slightly higher, 99.995%.

The results demonstrate that the gas-introducing mixer proposed by the inventive method for preparing ester of cyclohexane polycarboxylic acids from esters of benzene polycarboxylic acids is efficient to improve the contact between hydrogen gas and the reaction liquid even at low hydrogenation temperature.

Under the same hydrogenation conditions, Comparative Example 4 using the traditional impeller mixing device with the hydrogen nozzle got the conversion rate of diisononyl phthalate of 96.44%, and the yield of diisononyl cyclohexane phthalate of 95.01%, both inferior to Example 3. The results

TABLE 1

Reaction Conditions & Results for Examples and Comparative Examples

| | Example | | | | | | Comparative Example | | | | |
|---|---|---|---|---|---|---|---|---|---|---|---|
| | 1 | 2 | 3 | 4 | 5 | 6 | 1 | 2 | 3 | 4 | 5 |
| Hydrogen Introducing Device | | | | | | | | | | | |
| | Gas-Introducing Mixer having a hollow shaft to extract and exhaust hydrogen gas | | | | | | hydrogen nozzle | | | | |
| Diisononyl Phthalate (g) | 500 | — | 500 | — | — | — | 500 | — | 500 | 500 | — |
| Diisooctyl Phthalate (g) | — | 500 | — | 500 | 500 | 500 | — | 500 | — | — | 500 |
| Palladium Catalyst (g) | 5 | 5 | 5 | 5 | 2.5 | 5 | 5 | 5 | 5 | 5 | 5 |
| Hydrogen Gas (kg/cm$^2$) | 20 | 20 | 40 | 40 | 20 | 40 | 40 | 60 | 60 | 40 | 40 |
| Reaction Temperature (° C.) | 200 | 180 | 180 | 150 | 180 | 180 | 200 | 180 | 200 | 180 | 150 |
| Reaction Time (Hr) | 4 | 4 | 4 | 4 | 4 | 4 | 4 | 4 | 4 | 4 | 4 |
| Conversion Rate (%) | 100 | 99.98 | 100 | 99.20 | 99.92 | 100 | 95.12 | 95.47 | 97.31 | 96.44 | 90.52 |
| Yield (%) | 99.99 | 99.5 | 99.995 | 99.05 | 99.45 | 99.9 | 94.24 | 94.45 | 96.20 | 95.01 | 90.02 |

Note:
1. Conversion rate: [1 − (moles of remained ester of benzene polycarboxylic acid ÷ moles of input ester of benzene polycarboxylic acid)] × 100%
2. Yield: (moles of ester of cyclohexane polycarboxylic acid ÷ input esters of benzene polycarboxylic acid) × 100%

Result:

By comparing the results of Examples and Comparative Examples shown in Table 1, the following conclusions can be obtained:

1. Example 1 implemented the gas-introducing mixer with the hydrogen gas pressure of 20 kg/cm$^2$ and got the conversion rate of diisononyl phthalate of 100%, while the yield of diisononyl cyclohexane phthalate was 99.99%.

Comparative Example 1 implemented the traditional impeller mixing device with the hydrogen nozzle. Even though the hydrogen gas pressure was set at 40 kg/cm$^2$, the conversion rate of diisononyl phthalate was 95.12%, and the yield of diisononyl cyclohexane phthalate was 94.24%, both inferior to Example 1.

Comparative Example 3 further increased the hydrogen gas pressure to 60 kg/cm$^2$, and the conversion rate of diisononyl phthalate and the yield of diisononyl cyclohexane phthalate increased thereby still inferior to Example 1.

The results demonstrate that the method of the present invention for preparing esters of cyclohexane polycarboxylic indicate that even doubled hydrogen gas pressure would be useless to allow the traditional impeller mixing device with the hydrogen nozzle to improve the contact between hydrogen gas and the reaction liquid.

3. Example 6 adopted the same reaction conditions of hydrogenation as Example 3, except that diisooctyl phthalate was used instead. Example 6 showed a 100% conversion rate of diisooctyl phthalate, and a 99.9% yield of diisooctyl cyclohexane phthalate, similar to Example 3. The results indicate that the method of the present invention for preparing esters of cyclohexane polycarboxylic acids from esters of benzene polycarboxylic acids is applicable when different esters of benzene polycarboxylic acids are to be hydrogenated to produce esters of cyclohexane polycarboxylic acids, presenting equal effects.

4. Example 2 and Comparative Example 2 had similar hydrogenation conditions except that the hydrogen gas pressure of Example 2 was 20 kg/cm$^2$, and that of Comparative Example was 60 kg/cm$^2$. As observed, in respect of both the conversion rate of diisooctyl phthalate and the yield of diisooctyl cyclohexane phthalate, Example 2 was superior to Comparative Example 2. This indicates that the gas-introducing mixer of the present invention is of help to improve the contact between hydrogen gas and the reaction liquid. Even with the reduced hydrogen gas pressure, the inventive method for preparing ester of cyclohexane polycarboxylic acids from esters of benzene polycarboxylic acids is effective in increasing the yield of the ester of the cyclohexane polycarboxylic acid.

5. Example 5 had similar hydrogenation conditions to those of Example 2, except that Example 5 halved the amount of the palladium catalyst. Example 5 has the conversion rate of diisooctyl phthalate and the yield of diisooctyl cyclohexane phthalate similar to those of Example 2. This indicates that the inventive method for preparing ester of cyclohexane polycarboxylic acids from esters of benzene polycarboxylic acids helps to save the catalyst, leading to the advantage of saving costs.

6. Under identical hydrogenation conditions, Example 4 had the conversion rate of diisooctyl phthalate and the yield of diisooctyl cyclohexane phthalate obviously better than those of Comparative Example 5. This indicates that the inventive method for preparing ester of cyclohexane polycarboxylic acids from esters of benzene polycarboxylic acids allows hydrogenation for esters of benzene polycarboxylic acids under a lower temperature.

What is claimed is:

1. A method for preparing an ester of a cyclohexane polycarboxylic acid from an ester of a benzene polycarboxylic acid, comprising steps of:
   a) preparing a hydrogenation tank that is provided therein with a gas-introducing mixer capable of extracting and exhausting air and stirring;
   b) placing a reaction liquid made from an ester of benzene polycarboxylic acid into the hydrogenation tank;
   c) adding a hydrogenation catalyst that is one selected from a ruthenium catalyst, a palladium catalyst, a platinum catalyst and a rhodium catalyst in an amount of 0.1-5.0 wt % based on the ester of the benzene polycarboxylic acid;
   d) introducing a hydrogen gas with a pressure of 5-60 kg/cm$^2$;
   e) starting the gas-introducing mixer to make a hollow rotatory shaft of the gas-introducing mixer and vanes attached to a terminal of the rotatory shaft rotate at a predetermined speed to let the hydrogen gas be drawn into the hollow rotatory shaft through air-extracting holes formed on the hollow rotatory shaft above a liquid surface of the reaction liquid, and then exhausted out from air-exhausting holes formed on the hollow rotatory shaft at a location immersed in the reaction liquid, for having the hydrogen gas evenly distributed over the reaction liquid as the vanes stirring the reaction liquid;
   f) performing hydrogenation at 100-200° C. for 2 to 5 hours to hydrogenate the ester of the benzene polycarboxylic acid into the ester of the cyclohexane polycarboxylic acid; and
   g) after the hydrogenated reaction, cooling the reaction liquid to the room temperature, filtering out the catalyst and optionally further removing the solvent to obtain the ester of the cyclohexane polycarboxylic acid with a yield of 99.0-99.995%.

2. The method of claim 1, wherein the hydrogenation tank has a plate heat exchanger or a coil pipe.

3. The method of claim 1, wherein the hydrogenation catalyst is added in the amount of 0.5-1.0 wt % based on the ester of the benzene polycarboxylic acid.

4. The method of claim 2, wherein the hydrogenation catalyst is added in the amount of 0.5-1.0 wt % based on the ester of the benzene polycarboxylic acid.

5. The method of claim 3, wherein the pressure of the hydrogen gas is 20-40 kg/cm$^2$.

6. The method of claim 3, wherein the hydrogenation is performed at 180-200° C.

7. The method of claim 3, wherein the hydrogen gas is a pure hydrogen gas or a hydrogen gas containing an inert gas.

8. The method of claim 3, wherein the vanes of the gas-introducing mixer are plate vanes, curved vanes or vanes with grooves.

9. The method of claim 4, wherein the pressure of the hydrogen gas is 20-40 kg/cm$^2$.

10. The method of claim 4, wherein the hydrogenation is performed at 180-200° C.

11. The method of claim 4, wherein the hydrogen gas is a pure hydrogen gas or a hydrogen gas containing an inert gas.

12. The method of claim 4, wherein the vanes of the gas-introducing mixer are plate vanes, curved vanes or vanes with grooves.

* * * * *